United States Patent [19]

Seon

[11] Patent Number: 5,407,805

[45] Date of Patent: Apr. 18, 1995

[54] MONOCLONAL ANTIBODY REACTIVE TO VARIOUS HUMAN LEUKEMIA AND LYMPHOMA CELLS AND METHODS OF USING SAME FOR DIAGNOSIS AND TREATMENT

[75] Inventor: Ben K. Seon, Williamsville, N.Y.

[73] Assignee: Health Research, Inc., Buffalo, N.Y.

[21] Appl. No.: 848,911

[22] Filed: Mar. 10, 1992

Related U.S. Application Data

[63] Continuation-in-part of Ser. No. 359,505, Jun. 1, 1989, abandoned.

[51] Int. Cl.$^6$ .......... C07K 15/28; C12N 5/20; G01N 33/574
[52] U.S. Cl. .............. 435/7.23; 435/70.21; 435/172.2; 435/240.27; 530/388.7; 530/388.73
[58] Field of Search ........... 424/1.1, 9, 85.8, 85.91; 435/7.23, 7.9, 70.21, 172.2, 240.27; 436/548, 813; 530/388.7, 388.73, 391.3, 391.7

[56] References Cited

U.S. PATENT DOCUMENTS

| | | | |
|---|---|---|---|
| 4,671,958 | 6/1987 | Rodwell et al. | 424/85 |
| 4,724,212 | 2/1988 | Epstein | 435/240.27 |
| 4,724,213 | 2/1988 | Epstein | 435/240.27 |
| 4,831,117 | 5/1989 | Uckun | 530/387 |
| 4,904,596 | 2/1990 | Hakomorj | 435/240.27 |
| 4,939,083 | 7/1990 | Fukuda et al. | 435/7.23 |
| 5,096,810 | 3/1992 | Schwarting et al. | 435/7.23 |

FOREIGN PATENT DOCUMENTS 0173494 3/1986 European Pat. Off. .

OTHER PUBLICATIONS

Matsuzaki et al, Cancer Rsch., 47; 2160–2166 (1987).
Hara et al, Cancer Rsch., 48; 4673–4680 (1988).
Raso et al, Cancer Rsch. 42; 457–464 (1982).
Hood et al, Immunology, 2nd Ed., Benjamin Cummings Publishing Co., Inc., Menlo Park, Calif., 1984, pp. 66–68.
Nairn, Fluorescent Protein Tracing, Churchill Livingston, Edinburgh, 1976 pp. 301–303.
Stedman's Medical Dictionary, 24th Ed., Williams and Wilkins, Baltimore, 1982, pp. 777–778.
Negoro and Seon, Cancer Rsch., 41; 2973–2976 (1981).
Seon et al, J. Immunol., 127; 258–2588 (1981).
Seon et al, Proc. Nat. Acad. Sci. USA, 80; 845–849 (1983).
Seon et al, J. Immunol., 132; 2089–2095 (1984).
Haruta and Seon, Proc. Nat. Acad. Sci. USA, 83; 7898–7902 (1986).
L. M. Nadler et al, Jour. Clinical Invest., 67, 134–140, 1981.
L. M. Nadler et al, Jour. Immunology, 131, 244–250, 1983.
J. B. Peter, Use and Interpretation of Tests in Clinical Immunology, Interstate Press, Omaha, 1990, p. 23.
Coulter Immunology Catalogue, 1985, pp. 11–12 and 26.

Primary Examiner—David Saunders
Attorney, Agent, or Firm—Michael L. Dunn; Mark G. Bloom

[57] ABSTRACT

A novel hybrid cell line, designated T6-1G9, for production of monoclonal antibodies specific for a unique cell surface epitope associated with a wide variety of human lymphomas and leukemias. Hybridoma T6-1G9 was generated by fusing mouse myeloma cells with spleen cells from a BALB/c mouse that was immunized with a human leukemia antigen preparation isolated from the cell membranes of acute lymphoblastic leukemia cells. This invention also provides a method for producing the new monoclonal antibody designated SN7 and to diagnostic procedures using SN7 to detect various leukemias and lymphomas. Also disclosed are methods of using SN7 or reactive fragments of SN7 for the treatment of leukemia-lymphoma patients.

2 Claims, 3 Drawing Sheets

MONOCLONAL ANTIBODY REACTIVE TO VARIOUS HUMAN LEUKEMIA AND LYMPHOMA CELLS AND METHODS OF USING SAME FOR DIAGNOSIS AND TREATMENT

This is a continuation-in-part of application Ser. No. 07/359,505, filed Jun. 1, 1989, and now abandoned.

The invention described herein was made in the course of work done under the support of a PHS GRANT CA 19304 awarded by the National Cancer Institute.

TECHNICAL FIELD

This invention relates generally to hybridoma cell lines and monoclonal antibodies produced therefrom. More specifically, this invention relates to a novel hybridoma cell line that produces a monoclonal antibody reactive with a wide variety of human leukemias and lymphomas, to the monoclonal antibody generated from the hybridoma cell line, and to methods of using the monoclonal antibody, in whole or in part, for the diagnosis and therapy of various human leukemia-lymphomas.

DESCRIPTION OF THE PRIOR ART

Kohler and Milstein reported the first successful use of cell hybridization technology in generating continuously growing hybrid cell lines (called "hybridomas") that produce monoclonal antibodies [*Nature*256:4-95–497 (1975)]. Monoclonal antibodies (mAbs) are homogeneous antibodies which exhibit selective binding to a single antigenic determinant.

MAbs have significant advantages over conventional antisera with respect to specificity and availability. This is particularly so for mAbs directed to cell surface antigens [see e.g., *Curr. Top. Dev. Biol.* 14:1–32 (1980)].

Since 1975, much effort has been exerted by a number of investigators to generate hybridomas that produce mAbs directed to human leukemia-lymphoma (HLL) associated cell surface antigens. Several researchers, including the inventor herein, have successfully generated such anti-HLL mAbs. These mAbs include those directed to common ALL (acute lymphoblastic leukemia) antigen termed CALLA (CD10; a neutral endopeptidase), human thymus-leukemia antigens (CD1), T leukemia antigens and a lymphocytic-myelocytic leukemia associated antigen termed GP160.

Most of these mAbs, excepting those generated by the inventor herein, were produced by the conventional approach, i.e., by using intact HLL cells for immunizing mice to provide spleen cells for cell fusion. Despite the success described above, it is still difficult to generate anti-HLL mAbs by the conventional approach. This is probably because HLL-associated cell surface antigens are, in general, relatively minor cell surface components and poorly immunogenic as compared to other known major cell surface components such as HLA class I antigens.

The use of purified, isolated cell membrane antigens, rather than intact cells for immunizing mice should result in the production of mAbs with a greater affinity for relatively weak immunogens, e.g., HLL associated cell surface antigens, because of the absence of antigenic competition with strong immunogens, e.g., HLA class I antigens, during the immune response. Further, such use may give rise to a new group of mAbs that have not been obtained by using whole cells, i.e., those directed to antigenic determinants which are unable to induce an immune response when they are on intact cells.

In this regard, the present inventor previously developed a novel procedure for isolating relatively large quantities (submilligrams) of immunologically active HLL associated cell membrane antigens [*Cancer Research* 41:2973–2976 (July 1981); *J. Immunol.* 127:2580–2588 (1981)]. Using such antigen preparations, several mAbs directed toward several different HLL associated antigens have been generated [e.g., *Proc. Natl. Acad. Sci. USA* 80:845–849 (1983); *J. Immunol.* 132:2089–2095 (1984); *Proc. Natl. Acad. Sci. USA* 83:7898–7902 (1986)]. However, these mAbs are different from the mAb reported in this patent application.

During the past decade, remarkable progress has been made in the classification and characterization of HLL. MAbs have made a great contribution to this progress. Furthermore, mAbs have been extensively used for the diagnosis and follow-up of HLL patients.

However, successful utilization of mAbs for therapy of HLL has been very limited. An ideal mAb for such purposes will be one that reacts with 100% of the malignant cells for all HLL specimens but does not react with any of the normal cells or normal tissues.

Examples of antibodies which do not meet the desired criteria are for example described in Matsuzaki et al., *Canc. Rsch.*, 47, pp 2160–2166 (1987); Haruta et al, *Proc. Natl. Acad. Sci. USA*, 83, pp 7898–7902 (1986); Epstein, U.S. Pat. No. 4,724,213; Epstein, U.S. Pat. No. 4,724,212; Uckun, U.S. Pat. No. 4,831,117; and Roso et al., *Canc. Rsch.*, 42, pp 457–464 (1982).

This inventor has produced and characterized many mAbs which show various degrees of reactivity with HLL cells. Most of these anti-HLL mAbs were generated by using antigen preparations isolated from cell membranes using the above-mentioned procedure. Some of the mAbs generated showed remarkably high tumor specificity. However, because of their narrow specificity, some of these highly selective anti-HLL mAbs have only limited therapeutic utility. For instance, the mAb, designated SN1, reacts only with T acute lymphoblastic leukemia (T ALL) cells among many malignant and nonmalignant cell and tissue specimens tested. Although this antibody may be suitable for the in vivo therapy of T ALL patients, SN1 would have only limited therapeutic utility because T ALL has a low incidence among the general population. Therefore, the need remains for mAbs which strongly react with many different types of HLL but show a relatively low reactivity with normal cells, particularly normal bone marrow progenitor cells.

BRIEF DESCRIPTION

DETAILED DESCRIPTION OF THE INVENTION

Figure 1:
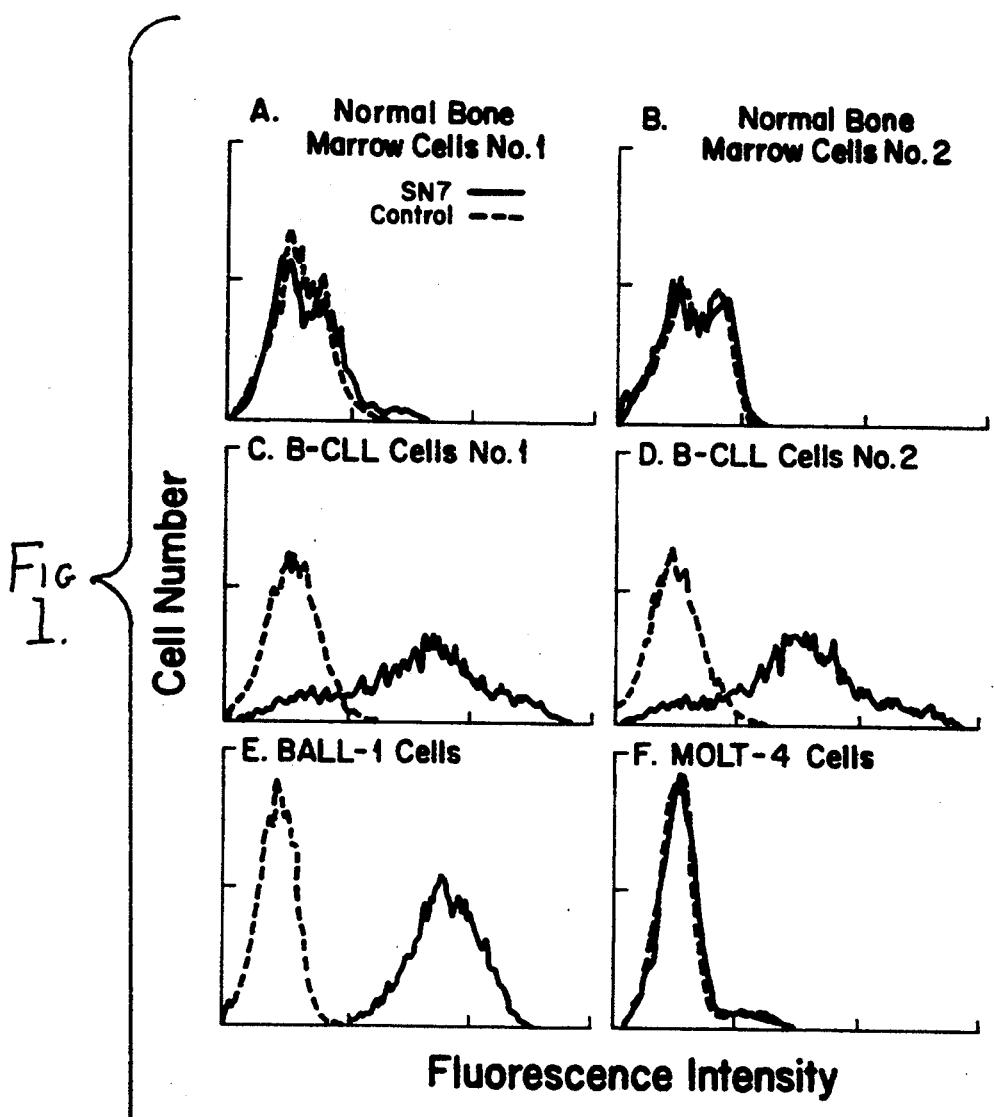
FIG. 1 depicts the graphic results of FACS analysis of the SN7 monoclonal antibody with selected human cell specimens.

The present invention provides a new mAb designated SN7 and/or a reactive fragment of SN7 which binds or reacts with a wide variety of human leukemia-lymphoma cells including one or more, and preferably a plurality and more preferably a majority of the following leukemia lymphoma cell specimens: human B chronic lymphocytic leukemia cells; B prolymphocytic leukemia cells; Hairy cell leukemia cells; non-T/non-B acute lymphoblastic leukemia cells; B acute lymphoblastic leukemia cells; acute myelocytic leukemia cells; acute myelomonocytic leukemia cells; acute monocytic leukemia cells; chronic myelocytic leukemia cells and non-Hodgkin's lymphoma cells.

This invention further provides conjugates of SN7 and/or a reactive fragment of SN7, through direct or indirect attachment or complexation, with one or more compounds including, but not limited to the following: drugs, toxins or fragments thereof, growth modifying biological response modifiers, enzymes, liposomes, radioactive agents, photodynamic agents, anti-idiotype antibodies or fragments thereof, chimeric antibodies or fragments thereof,, monoclonal antibodies or fragments thereof and other antibodies and their fragments.

As is well known in the art, a "reactive fragment" includes any antigen-binding fragment of an Ig molecule including Fab, F(ab')$_2$, Fab' or Fv fragments. Ig includes immunoglobulin molecules including IgG, IgM, IgA, IgD and IgE.

The present invention further provides a new hybridoma cell line designated T6-1G9 which is generated by fusing mouse myeloma cells with spleen cells from a mouse or other suitable animal immunized with a human non-T leukemia antigen preparation isolated from cell membranes of human acute lymphoblastic leukemia cells. The hybridomas thus produced are screened for those with culture supernatants containing antibody which give selective binding to HLL cells. The desired hybridomas are subsequently cloned and characterized.

This invention still further provides a method for preparing mAb SN7 or a reactive fragment of SN7 which comprises culturing hybridoma cell line T6-1G9 in a suitable medium and recovering the mAb or reactive fragment from the culture supernatant of said hybridoma cell line. Alternatively, mAb SN7 or a reactive fragment of SN7 may be generated by injecting hybridoma cell line T6-1G9 into an appropriate animal and recovering the antibody or reactive fragment from the malignant ascites or serum of the animal so injected.

This invention is further directed to diagnostic and therapeutic methods employing mAb SN7 in the treatment of various human leukemias and lymphomas.

MAb, SN7, was tested against a variety of cultured and uncultured human cell specimens using a cellular radioimmunoassay and/or FACS analysis. Based on the information obtained from this analysis, SN7 was shown to bind or react with uncultured human B chronic lymphocytic leukemia cells; B prolymphocytic leukemia cells; Hairy cell leukemia cells; non-T/non-B acute lymphoblastic leukemia cells; B acute lymphoblastic leukemia cells; acute myelocytic leukemia cells; acute myelomonocytic leukemia cells; acute monocytic leukemia cells; chronic myelocytic leukemia cells and non-Hodgkin's lymphoma cells. SN7 did not react with any T acute lymphoblastic leukemia cell specimens tested. The results of the reactivity with various cultured human cell lines generally agreed with the above-mentioned reactivity with the uncultured cell specimens.

The reactivity of SN7 with several different normal (or nearly normal) bone marrow specimens was either not significant or only weakly positive for a minor population of some bone marrow specimens. The bone marrow specimens used were derived from several different leukemia-lymphoma patients in remission. Of normal peripheral blood cells, T cells, granulocytes, erythrocytes and platelets showed no-significant reactivity with SN7. ("No significant reactivity" is defined as that which is undetectable using a cellular radioimmunoassay (RIA), because the level of activity detected cannot be distinguished over usual background control levels.) However, SN7 showed varying degrees of weak reaction with a subpopulation of normal peripheral blood B cells and monocytes. The degree of the reactivity shown varied depending upon the donors of the peripheral blood.

SN7 was found to be an IgG1-k antibody. A single major component of approximately 20,00 daltons was detected when glycoprotein mixtures isolated from HLL cell membranes were subjected to conventional immunoprecipitation using SN7.

Numerous methods have been employed during recent years for attaching or conjugating a variety of molecules to various sites on antibodies and in particular monoclonal antibodies directed against any desired target antigen. One such method is disclosed in U.S. Pat. No. 4,671,958, the disclosure of which is incorporated by reference herein. The monoclonal antibody of the present invention has been found to be sufficiently stable to undergo known conjugation procedures with other agents. Numerous bioactive agents may be conjugated to the mAb in accord with the present invention including drugs, toxins or toxin fragments, growth modifying biological response modifiers enzymes, liposomes, radioisotopes, photodynamic agents, or other antibodies including anti-idiotype antibodies, chimeric antibodies and monoclonal antibodies or fragments of such antibodies. In addition, the mAb or fractions of these mAbs may be incorporated into other matrices for use in separation schemes which are based upon antibody-antigen reactions. A multitude of known carrier or conjugating agents: is disclosed in U.S. Pat. No. 4,671,958 and any of these agents would be suitable for binding to the antibodies disclosed herein or to active fragments of the antibody disclosed herein, namely F(ab')$_2$, Fab, Fab' or Fv fragments without significant loss of antibody activity.

Numerous drugs may be complexed with the antibody of the present invention. In general, when such drugs are used for detecting or treating leukemia or lymphoma cells, such drugs are cytotoxic agents such as methotrexate as for example described by Endo et al., *Cancer Res.*, V. 48, pp 3330–3335, Jun. 15, 1988 or daunorubicin as for example described by Biddle et al., *Leukemia Res.*, V. 13, No. 8, pp 699–707, 1989; both of which are incorporated herein by reference.

The antibody of the present invention may similarly be complexed with toxins, desirably those which are especially effective against cancer cells, by methods well known to those skilled in the art. The antibody may, for example, be complexed with Pseudomonas exotoxin by methods similar to those described by Fitzgerald et al., *Proc. Natl. Acad. Sci. USA*, Vol. 84, pp 4288–4292, Jun. 1987, incorporated herein by reference or for example with Ricin or the Ricin A chain fragment, as subsequently described herein.

The antibody of the present invention may be complexed with growth modifying biological response modifiers, especially those which suppress cell growth when the complex is to be used in cancer treatment.

Such biological response modifiers may be broadly considered to have hormone-like activity and as such may be broadly classified as hormones. Suitable biological response modifiers or hormones for forming such complexes with antibodies are known to those skilled in the art and for example include interleukins, interferons, growth factors, and lymphokines. Such complexes have utility in cancer management as aids for both cell targeting and growth control.

Methods for forming such complexes are, for example, with respect to interleukin 2, described by Fell et al., *Journal of Immun.*, 146, pp 2446–2452, Apr. 1, 1991, and with respect to growth factors such as TNF, described by Foon, *Cancer Rsch.*, 49, 1621–1639. Both of these articles are incorporated herein by reference.

Complexes may be formed between the antibody of the present invention and radioactive agents. Methods for forming complexes between antibodies and radioactive agents are well known and an example of such a method is subsequently described herein.

Complexes may also be formed between enzymes and the antibody of the invention. Alkaline phosphatase and cytosine phosphatose enzymes suitable for forming complexes with antibodies are, for example, described by Senter, *FASEB Journal*, Vol. 4, pp 188–193, Feb. 1990, incorporated herein by reference.

The antibodies of the present invention may be complexed with photodynamic agents. Methods for complexing antibodies with photodynamic agents are well known in the art. Methods for forming complexes with photodynamic agents such as porphorins are, for example, described by Jiang et al., *Journal Natl. Can. Inst.*, Vol. 83, pp 1218–1219, Sep. 1991, incorporated herein by reference.

The antibody of the present invention may be complexed with other antibodies or fragments to increase targeting ability (bispecific antibodies) or to utilize the additional antibody to achieve a desired cancer cell response, e.g., to more efficiently bring cytotoxic T cells to tumor cells. Methods for forming complexes between antibodies are well known in the art. Such a method, with respect to formation of a bispecific antibody is, for example described by Forger et al., *Immun. Today*, Vol. 12, pp 51–53, 1991, incorporated herein by reference. These methods apply regardless of the source of the antibody or fragment. For example, as later additionally discussed herein, anti-idiotype antibodies and fragments, chimeric antibodies and fragments, and monoclonal antibodies or fragments may be complexed with the antibody of the present invention using generally known complexing methods. Examples of fragments, for example, include the well known IgG fragments F(ab')2, Fab, Fab' and Fv. Such fragments may be obtained by cleaving IgG or may be prepared directly, e.g., as described by Ornatowska, Mol, *Immun.*, Vol. 28, No. 4/5, pp 383–391, 1991, incorporated herein by reference.

"Fragments" as used herein means a section of a larger intact antibody, which section continues to contain desired recognition sequences. Such fragments in that sense may, in themselves, be considered antibodies and the term "antibody" may be considered to include such fragments. The term "antibody" is also intended to encompass antibodies and fragments of broad source and type, e.g., monoclonal antibodies and fragments, anti-idiotype antibodies and fragments and chimeric antibodies and fragments.

MAb SN7 has been conjugated with the A chain of ricin, a plant toxin. The conjugate has demonstrated the ability to selectively kill HLL cells, including B leukemia lymphoma cells, which express the epitope defined by SN7. Such procedures include covalently attaching or complexing the mAb or a fragment thereof to the agent or drug of interest either directly or indirectly using a suitable linking agent. Other mAbs, SN1, SN2, SN5 and SN6, also identified by the inventor herein, when conjugated with the ricin A-chain (RA), have demonstrated highly specific killing capability for leukemia cells as reported in *Cancer Research* 44:259–264 (1984), *Proc. Natl. Acad. Sci.* USA 84:3390–3394 (1987), and *Cancer Research* 48:4673–4680 (1988), the disclosures of which are incorporated by reference herein. Such conjugated SN1, SN2, SN5 and SN6 MAbs have been found to be effective against T or Non T / Non B leukemia cells, but not against B leukemia lymphoma cells. This is especially important since B type leukemia and lymphoma are the most common.

In order to prepare effective immunoconjugates using a mAb, in most cases, the mAb needs to be effectively internalized, i.e., enter into the target cells after binding to a cell surface antigen. Indeed, SN7 is effectively internalized into target HLL cells after SN7 binds to the cell surface antigen on HLL cells.

In addition, the antibody of the present invention may be made cytotoxic in a complement-mediated cytolysis by adding rabbit anti-mouse IgG antibodies.

The foregoing and additional advantages and characterizing features of the present invention will become clearly apparent upon a reading of the ensuing detailed description together with the included examples.

Materials and Methods

The monoclonal antibodies exhibiting utility in the present invention were prepared generally following the procedures of Kohler and Milstein as reported in *Nature*, 256:495–97 (1975).

The details of the process are well known in the art. Briefly, the process involves injecting a mouse, rat, or other suitable animal, with an antigen. The animal is subsequently sacrificed and cells from its spleen are fused with cells of continuously replicating tumor cells, e.g., myeloma or lymphoma cells. After fusion, three cell types remain in culture: splenocytes, myeloma cells and hybrids. The splenocytes and myeloma cells die off and the hybrid cells begin to double every 24–48 hours. The result is the production of a hybrid cell line, hybridoma, that reproduces in vitro. The population of hybridomas are screened to identify individual classes each of which secrete a single antibody specific for a desired antigen.

The antigen preparation was isolated from cell membranes leukemia cells derived from a patient with non-T/non-B type ALL (B-lineage i.e., immature B cells which do not express either typical T antigen or B antigen markers). The procedures used were recently described in *Proc. Natl. Acad. Sci.* USA, 83:7898–7902 (1986). The procedures were based on a modification of an earlier method for isolating human T leukemia antigen preparations as disclosed in *J. Immunol.*, 127:2580–2588 (1981); *Proc. Natl. Acad. Sci.* USA, 80:845–849 (1983); and *J. Immunol.*, 132:2089–2095 (1984), the disclosures of which are incorporated by reference herein.

EXPERIMENTAL EXAMPLE

Production of Monoclonal Antibodies

A. Leukemia Antigen Preparation

The immunizing antigen preparation was produced as follows: Cell membranes of leukemia cells derived from a patient with non-T/non-B type (B-lineage) ALL were prepared by mechanical disruption of the cells followed by differential centrifugations of the disrupted cells. The membrane proteins were solubilized by deoxycholate treatment in the presence of recrystallized iodoacetamide (final concentration, 5 mM) and fractionated by affinity chromatography on serially connected columns of Lens culinaris lectin (LcH) and Ricinus communis lectin (RCA). The LcH-bound and RCA-bound glycoconjugates (mostly glycoproteins) were individually eluted, combined and subjected to passive immunoaffinity chromatography; i.e., the fractions were passed through three serially-connected immunoadsorbent columns. The immunoadsorbents consist of affinity-purified rabbit anti-human $\beta_2$-microglobulin antibodies coupled to Sepharose CL4-B, rabbit anti-human normal B cell antibodies coupled to Sepharose CL4-B and rabbit anti-human normal peripheral blood lymphocyte antibodies coupled to Sepharose CL4-B. Materials in the pass-through fractions from the above three-columns were pooled, concentrated and the passive immunoaffinity chromatography was repeated once.

B. Immunization and Somatic Cell Hybridization

1. Immunization

A mouse was immunized subcutaneously (s.c.) with 30 μg of the cell membrane antigen preparation in 0.12 ml of 10 mM Tris-HCl buffer, pH 8.0, containing 0.3 percent deoxycholate (Tris-DOC buffer) mixed with an equal volume of Freund's complete adjuvant. In addition, $2 \times 10^9$ Bordetella pertussis bacteria were injected s.c. A booster immunization was carried out by injecting s.c. 15 μg of the antigen preparation mixed with Freund's incomplete adjuvant. Another booster immunization was performed by injecting i.p./i.v. (intraperitonealy/intravenously) 60 μg (in 0.1 ml of Tris-DOC buffer) of the antigen preparation mixed with 0.4 ml of saline. The spleen was taken for the cell fusion 3 days after the last immunization.

2. Cell Hybridization

For the cell fusion, spleen cells ($1 \times 10^8$ cells) derived from the immunized mouse were fused with P3/NS1/1-Ag4-1 (abbreviated as NS-1) murine myeloma cell line ($4 \times 10^7$ cells) using polyethylene glycol [*Nature* 226:550–552 (1977)]. The NS-1 myeloma cell line was obtained from the Cell Distribution Center of the Salk Institute, San Diego, Calif. The fused cells were washed and centrifuged. The washed cell pellet was suspended in 200 ml of hypoxanthine-aminopterine-thymidine (HAT) medium and 1 ml of the cell suspension was placed in each of the wells of eight 24-well (3.5 ml capacity per well) tissue culture plates (Linbro Division, Flow Laboratories, Inc.). Each well already contained $2 \times 10^5$ cells of BALB/c mice peritoneal exudate cells in 0.2 ml of HAT medium as feeder cells. The cells were cultured in a $CO_2$ (5 percent) incubator at 37° C. One-half of the culture medium of each well was replaced with fresh HAT medium twice a week. On day 12 after the cell fusion, the initial screening test was carried out using a radioimmunoassay to identify the cultured supernates containing the desired antibody.

3. Screening and Cloning of Hybridoma

Monoclonal anti-leukemia antibodies in the culture supernatants of the hybridomas were screened by a radioimmunoassay (see below). Cloning of hybridomas was carried out by propagating from a single cell by means of limiting dilution [*Selected Methods in Cellular Immunology* (B. B. Mischell and S. M. Shiigi, Eds.) pp. 351–372; Freeman and Company, San Francisco, 1980]. To ensure the monoclonality of the clone, the hybridoma clone resulting from the first cloning was subjected to recloning.

Characterization of SN7 Reactivity

A. Microscale Radioimmunoassay

It should be noted that Fc receptors on the target cells are blocked with human IgG during the assay.

1. Preparation of F (ab')$_2$ of Affinity-Purified Goat Anti-Mouse IgG Antibodies To establish an efficient, sensitive radioimmunoassay, the F (ab')$_2$ fragment of affinity-purified goat anti-mouse IgG antibodies was first prepared as follows: The IgG of goat anti-mouse IgG antiserum was digested with pepsin [*Arch. Biochem. Biophys.* 89:230–244 (1960); *Immunochemistry* 13:407–415(1976)] and the digest was fractionated on a Sephadex G-150 column [*Immunochemistry* 13:407–415 (1976)]. The resultant F(ab')$_2$ fragment was passed through an immunoadsorbent column prepared with Sepharose CL4-B conjugated with human IgG. This treatment was carried out to remove any F(ab')$_2$ components which react with antigenic determinants common to mouse IgG and human IgG. This treatment is important when the F(ab')$_2$ is tested in the presence of human cells (see below). The unbound F(ab')$_2$ was applied to an immunoadsorbent column prepared with mouse IgG coupled to Sepharose CL4-B and the column washed. The bound goat F(ab')$_2$ was eluted with 0.1M glycine-HCl buffer, pH 2.6, containing 0.2 M NaCl, 1 mM EDTA and 0.03 percent $NaN_3$. This eluted F(ab')$_2$ was found to consist of only the monomer form and not to contain any significant amount of aggregates of F(ab')$_2$ as demonstrated by gel filtration on a Sepharose CL-6B column. This F(ab')$_2$ fragment preparation of specific goat antibodies directed to mouse IgG [designated as F(ab')$_2$-G$\alpha$MIgG] was used for radioimmunoassay after being radiolabeled with carrier-free $^{125}$I by the IODO-GEN method. [*Biochemistry* 17:4807–4817 (1978); *Biochem. Biophys. Res. Commun.* 80:849–857 (1978); *J. Immunol.* 127:2580–2588 (1981)]. The quantitative binding test using this $^{125}$I-F(ab')$_2$-G$\alpha$MIgG against purified mouse IgG showed that below ng quantities of mouse IgG antibodies could be determined by using this radiolabeled antibody reagent. The present antibody reagent was found to react with mouse IgM almost as efficiently as with mouse IgG.

2. Radioimmunoassay

Using the $^{125}$I-F(ab')$_2$-G$\alpha$MIgG, a microscale radioimmunoassay was employed to determine the reactivity of mAbs with various cells. In a typical assay, triplicate 20-μl aliquots of various dilutions of culture fluids or ascites of hybridomas and $2$–$10 \times 10^5$ cells in 10 μl of Hepes (pH 7.3) buffer containing 0.1 percent of human IgG were incubated in individual wells of 96-well microtiter plates (Cooke Engineering Co.) for 60 min at 4° C. with continuous shaking. The Hepes buffer consisted of RPMI1640 medium containing 25 mM N-2-hydroxyethyl-piperazine-N'-2-ethanesulfonate (Hepes), 0.5 percent bovine serum albumin, Trasylol (50 kallikrein units/ml) and 0.1 percent NaN$_3$. The human IgG is added to the Hepes buffer to minimize non-immunospecific binding (both biospecific, e.g., Fc receptor, and non-biospecific) of mouse antibodies and $^{125}$I-labeled F(ab')$_2$-GαMIgG to the cells during the radioimmunoassay. In addition, the microtiter plate wells were treated before use with the Hepes buffer.

The mixtures were centrifuged at 500×g and 4° C. for 10 minutes and the pelleted cells washed three times. Approximately 2ng (3–5×10$^4$ cpm) of the $^{125}$I-F(ab')$_2$ in 10 μl of Hepes buffer were added to each washed pellet and the reaction mixtures incubated with shaking and washed as described above. The radioactivity in the washed pellet was determined in a gamma-ray spectrometer. When platelets are used as targets, the radioimmunoassay is carried out in conical polypropylene tubes (1.5 ml size) instead of microtiter plates because it is necessary to precipitate platelets at significantly higher centrifugal force, (e.g., 2500×g).

Three different kinds of controls were included for individual cell specimens. In the control sample (in triplicate) for hybridoma culture supernate, the culture supernate was replaced with either culture medium, culture medium containing mouse IgG (10 μg/ml) or culture medium containing mouse IgM (10 μg/ml). No significant difference was observed in the amounts of radioactivity detected in the three controls and the average value of these controls was subtracted from the radioactivity of test samples. As the control sample (in triplicate) for the dilutions of hybridoma ascites, the corresponding dilutions of appropriate control murine ascites containing mouse Ig of the same isotype as the hybridoma antibody were included [*Proc. Natl. Acad. Sci. USA* 80:845–849 (1983)].

A microscale radioimmunoassay using a microtiter plate is preferred since it is very sensitive, reproducible and objective. Further, a single test using this assay, permits the determination of 100 samples, in triplicate.

B. FACS Analysis

FACs analysis was carried out as follows. Cells (1.5 to 2 million) were suspended in 10 to 20 μl of RPMI 1640 medium containing 25 mM Hepes, 0.1% human IgG, 0.5% bovine serum albumin, 2 mM EDTA, Trasylol (50 kallikrein units/ml), and 0.1% NaN$_3$ (Buffer A) and allowed to stand for 30 min at 4° C. Then, the cells were incubated with 100 μl of hybridoma culture supernatant or an isotype-matching control mouse IgG solution (10 μg/ml) for 90 min at 4° C. After three washes with cold phosphate-buffered saline, the cells were incubated with fluorescein-conjugated F(ab')$_2$ fragment of sheep anti-mouse Ig (SaMIg) (Sigma, St. Louis, Mo.) for 90 min at 4° C. The incubated cells were washed 3 times with cold phosphate-buffered saline and suspended in 25 mM Hepes buffer, pH 7.2, in RPMI 1640 medium containing 2.5 mM EDTA and 5% fetal bovine serum. To fix the cells, 1 ml of the cell suspension was mixed with an equal volume of a 16% formaldehyde solution in RPMI 1640 medium. The fixed cells were kept in the cold room protected from the light until analyzed by FACS using a Becton Dickinson FACS 440. Each sample containing at least 10,000 cells was analyzed using the log amplification mode. Negative controls were target cells labeled with control mouse IgG and FITC-labeled second antibody, i.e., F(ab')$_2$-SaMIg.

C. Radioimmunoprecipitation and Sodium Dodecyl Sulfate Poly-acrylamide Gel Electrophoresis (SDS-PAGE)

LcH-bound glycoconjugate preparations were isolated from the cell membranes of uncultured malignant cells from two patients with CLL and two patients with non-Hodgkin's lymphoma as described above for the antigen preparation (See above Section A. Leukemia Antigen Preparation). Malignant cells from each of the two CLL patients were used separately to prepare glycoconjugate samples whereas malignant cells from the two non-Hodgkin's lymphoma patients were mixed and used for preparing a glycoconjugate sample.

The isolated glycoconjugates by this procedure are mostly glycoproteins. The three isolated glycoprotein preparations derived from the patients were separately radiolabeled with $^{125}$I using an IODO-GEN-coated Minisorp tube. To reduce the background radioactivity during the radioimmunoprecipitation, the three radiolabeled preparations were pretreated by incubating for 1 hour at 0° C. with Pansorbin (Calbiochem), which had been coated with affinity-purified rabbit anti-mouse IgG antibodies. For the specific immunoprecipitation, the pretreated radiolabeled samples were incubated, in duplicate, for 1 hour at 0° C. with Pansorbin coated with affinity-purified rabbit anti-mouse IgG antibodies (RαMIgG) and mAb SN7 (IgG1). Control immunoprecipitates were prepared by using Pansorbin coated with RdMIgG and control mAb (anti-HLA DR) or control mouse IgG1 (MOPC 195 variant). The specific and control immunoprecipitates were washed twice with Tris-HCl buffer (pH 7.2) containing 0.5% taurocholate (a detergent), 0.15M NaCl, 2 mM EDTA, 0.1% bovine serum albumin, Trasylol (100 kallikrein units/ml), and 0.05% NaN$_3$ (Tris/taurocholate buffer). The immunoprecipitates were further washed twice with Tris/Renex 30 buffer (Tris buffer containing 0.5% Renex 30, a nonionic detergent, instead of 0.5% taurocholate) and once with 0.0625M Tris-HCl buffer (pH 6.8) containing 0.01% cytochrome c. The radiolabeled antigens of the washed immunoprecipitates were released from the Pansorbin by boiling for 3 min in the presence of 2.5% SDS and in the presence or absence of 0.1% M dithiothreitol. The released antigens were analyzed by SDS-PAGE using standard procedures, and autoradiograph was prepared by using a Kodak X-OMAT AR film and X-Omatic intensifying screen.

Preparation and Testing of Immunoconjugates Containing SN7

A. Preparation of Immunoconjugates

The purified SN7 antibody was covalently conjugated with the A chain of ricin, a plant toxin derived from the castor bean. The conjugation was carried out by a procedure which is based on a modification of our previously reported procedure [*Cancer Research* 48: 4673–4680 (1988)]. Briefly, the purified SN7 antibody in phosphate-buffered saline (PBS, pH 7.4) was treated with a 20-fold molar excess of SPDP, a heterobifunctional crosslinker, for 30 min at room temperature to introduce 2-pyridyl disulfide groups into the antibody molecule. The modified and dialyzed antibody was then mixed with a three-fold molar excess of the purified, freshly reduced ricin A-chain (RA) in PBS containing 1 mM EDTA and incubated at 4° C. for 24 hr and at room temperature for 24 hr. The antibody-RA conjugates were separated from the unbound RA by gel filtration on a calibrated Sephacryl S-300 column. The remaining unconjugated antibody was removed from the conjugate fraction by chromatography on a Blue Sepharose column [*Analytical Biochemistry* 160: 440–443 (1987)].

B. Selective Killing of Human Leukemia-Lymphoma (HLL) Cells by. Immunoconjugates A direct test of in vitro cytotoxicity against target HLL cells and control cells was carried out as described previously [*Cancer Research* 44: 259–264 (1984)]. Briefly, cells were suspended in RPMI1640 medium supplemented with 5% fetal bovine serum, penicillin (100 units/ml), streptomycin (100 μg/ml) and gentamicin (50 μg/ml) to a cell concentration of $7.5 \times 10^5$ cells/ml. One-ml portions of the cell suspensions were placed in individual wells (approximately 3.5 ml capacity) of Linbro tissue culture plates. Immunoconjugates or PBS (control) was added, in triplicate, to the individual well cultures and the plates were placed in a humidified $CO_2$ (5%) incubator at 37° C. On days 2 and 3, a portion of each cell culture supernatant was replaced with fresh cell culture medium. A portion of each cell suspension was removed daily to determine viable cells using trypan blue.

The in vivo antitumor efficacy of SN7 immunoconjugate was evaluated by using NALM-6 human leukemia cells that were transplanted into athymic nude mice [*Cancer Research* 49: 706–710 (1989)]. Twenty nude mice (8 weeks old) which were inoculated i.p. with $6 \times 10^6$ of the in vivo adapted NALM-6 cells (day 0) were divided into 4 groups. Each of the four groups was administered i.p. with 1e) PBS (control), 2) 10 μg of control ricin A-chain (RA) conjugate, i.e., MOPC 195var-RA, 3) 10 μg of naked (unconjugated) mAb SN7, and 4) 10 μg of SN7-RA. The treatment was initiated 24 h (day 1) after the tumor inoculation and repeated by administering on day 2, 3, 4 and 21 for a total of 5 injections including the initial injection.

RESULTS

Initial Characterization of Monoclonal Antibody

Reactivity of culture supernatants of hybridoma primary cultures and hybridoma clones derived from the primary cultures were initially characterized using a cellular radioimmunoassay (RIA) with various cultured and uncultured cells. The reactivity of SN7 with various malignant human hematopoietic cell lines is summarized in Table 1.

TABLE 1

Reactivity of SN7 with malignant human hematopoietic cell lines
The reactivity was determined using 20 μl of a 5-fold dilution of culture fluid of hybridoma T6-1G9 and $2 \times 10^5$ cells in each test by means of a cellular radioimmunoassay.

| Cell line[a] | Origin of cell line | Degree of Reactivity |
|---|---|---|
| B cell | | |
| BALL-1 | ALL | ++++ |
| BALM-2 | ALL | ++++ |
| BALM-3 | lymphocytic lymphoma | ++ |
| BALM-5 | lymphocytic lymphoma | ++ |
| SU-DHL-4 | histiocytic lymphoma | ++++ |
| Daudi | Burkitt's lymphoma | ++++ |
| Raji | Burkitt's lymphoma | ++++ |
| Ramos | Burkitt's lymphoma | +++ |
| Pre-B cell | | |

TABLE 1-continued

Reactivity of SN7 with malignant human hematopoietic cell lines
The reactivity was determined using 20 μl of a 5-fold dilution of culture fluid of hybridoma T6-1G9 and $2 \times 10^5$ cells in each test by means of a cellular radioimmunoassay.

| Cell line[a] | Origin of cell line | Degree of Reactivity |
|---|---|---|
| NALM-1 | CML-Bc[b] | ++ |
| NALM-6 | ALL | ++ |
| Non-T/Non-B cell | | |
| KM-3 | ALL | ++++ |
| NALM-16 | ALL | + |
| T cell | | |
| MOLT-4 | ALL | − |
| JM | ALL | − |
| CCRF-HSB-2 | ALL | − |
| Ichikawa | ALL | − |
| HPB-MLT | LTL[c] | − |
| HUT 78 | Sezary syndrome | ++++ |
| Myeolo/monocytic cell | | |
| ML-2 | acute myelocytic leukemia | + |
| HL-60 | acute promyelocytic leukemia | − |
| U937 | histiocytic lymphoma | ++ |
| Myeloerythroid cell | | |
| K562 | CML-BC | − |
| Plasma cell | | |
| ARH-77 | Multiple myeloma | ++++ |
| HS | Multiple myeloma | +++ |
| RPMI 8226 | Multiple myeloma | + |

[a]cell lines are publicly known and publicly available, e.g., from Dr. Ben Seon, Reswell Park Cancer Institute.
[b]Chronic myelocytic leukemia in blast crisis
[c]Leukemic phase of T cell lymphoma SN7 strongly reacted with all B cell type HLL cell lines tested; these cell lines were derived from patients with ALL, lymphocytic lymphoma, histiocytic lymphoma and Burkitt's lymphoma. SN7 also reacted with 2 of the 2 pre-B HLL cell lines tested, 2 of the 2 non-T/non-B.(B-lineage) HLL cell lines tested, a T Sezary syndrome cell line and 2 of the 3 myelo/monocytic HLL cell lines tested. In addition, SN7 reacted with 3 of the 3 plasma cell lines derived from patients with multiple myeloma. However, SN7 did not react with 5 of the 6 T HLL cell lines tested, an immature promyelocytic leukemia cell line HL-60 nor with a myeloerythroid leukemia cell line K562. Further reactivity of SN7 was observed with 3 EB virus-transformed B cell lines CCRF-SB, RPMI 1788 and RPMI 8057.

SN7 showed minor or no significant reactivity against 7 normal (or near normal) bone marrow cell specimens derived from 7 different HLL patients in remission. The reactivity of SN7 with normal (or near normal) bone marrow cell specimens was further studied by FACS analysis and the results of FACS analysis were consistent with those of cellular RIA (see below). SN7 showed varying degrees of weak reactivity with 9 mononuclear cell specimens obtained from peripheral blood from 9 healthy donors. The reactivity of SN7 was further determined with different cell fractions obtained from normal peripheral blood. No significant reactivity of SN7 was observed with any T cell, granulocyte, erythrocyte or platelet fractions. However, varying degrees of a weak reaction of SN7 were observed with B cell and monocyte fractions. The degree of reactivity varied depending on the donor of the peripheral blood.

A comparison of the reactivity of SN7 with those of SN5, SN6, Lym-1, Lym-2 and B43 are set out in Table 2.

TABLE 2

Comparison of the reactivity of SN7
with those of SN5, SN6, Lym-1, Lym-2 and B43.

| Cell line | SN7 | SN5 | SN6 | Lym-1 | Lym-2 | B43 |
|---|---|---|---|---|---|---|
| B cell | | | | | | |
| BALL-1 | + | − | − | NT | NT | NT |
| BALM-2 | + | + | − | + | − | NT |
| SU-DHL-4 | + | NT | NT | − | + | NT |
| Daudi | + | + | − | NT | NT | NT |
| Ramos | + | NT | NT | − | − | NT |
| Pre-B cell | | | | | | |
| NALM-1 | + | + | + | − | NT | NT |
| NALM-6 | + | + | + | − | − | + |
| Non-T/non-B cell | | | | | | |
| KM-3 | + | + | + | − | − | NT |
| T cell | | | | | | |
| HPB-MLT | − | + | − | NT | NT | NT |
| HUT 78 | + | − | − | NT | NT | NT |
| Myelo/monocytic cell | | | | | | |
| ML-2 | + | − | + | − | − | NT |
| HL-60 | − | NT | + | − | − | − |
| U937 | + | NT | + | − | − | NT |
| Myeloerythroid cell | | | | | | |
| K562 | − | NT | − | − | − | + |

NT: Not tested.
SN5, Matsuzaki et al., Cancer Rsch., 47, pp 2160-2166, (1987).
SN6, Haruta et al., Proc. Natl. Acad. Sci. USA, 83, pp 7898-7902, (1986).
Lym-1, Epstein, U.S. Pat. No. 4,724,213.
Lym-2, Epstein, U.S. Pat. No. 4,724,212.
B43, Uckun, U.S. Pat. No. 4,831,117.
The reactivity of J5 (Raso et al., Cancer Rsch., 42, pp 457-464 (1982)) is same as that of SN5 and both monoclonal antibodies react with common acute lymphoblastic leukemia antigen (Matsuzaki et al., supra).
B43 was tested against only a few cell lines. Nevertheless, B43 is different from SN7 in the reactivity to K562 cell line. In addition, B43 did not react with any of 13 acute myelocytic leukemia (AML) specimens from patients whereas SN7 reacted with the majority (4 of 6) of AML specimens from patients. Furthermore, the antigen recognized by B43 is a proteolipid while the antigen recognized by SN7 is glycoprotein.
As shown above, SN7 is significantly different from each of SN5, J5, SN6, Lym-1, Lym-2 and B43.

Reactivity with Uncultured HLL Cells

The reactivity of SN7 with fresh (uncultured) cell specimens derived from 76 patients with various HLL was determined by a cellular RIA and the results are summarized in Table 3.

TABLE 3

Reactivity of SN7 with uncultured human
leukemia and lymphoma cells
Individual cell specimens were derived from peripheral
blood, bone marrow or lymph node of different patients. In the
cellular radioimmunoassay, three different controls were included
with each cell specimen. one of these was control mouse IgG1 (10
μg/ml) in the hybridoma culture medium in place of the culture
fluid of hybridoma. The other two controls were BALL-1 cells (a
positive control) and MOLT-4 cells (a negative control) in place
of the target cell specimen.

| Disease of Patient | Reactivity[a] |
|---|---|
| B chronic lymphocytic leukemia | 23/23 |
| B prolymphocytic leukemia | 6/6 |
| Hairy cell leukemia | 4/6 |
| Non-T/non-B ALL[b] | 7/10 |
| B ALL | 1/1 |
| T ALL | 0/5 |
| Acute myelocytic leukemia | 4/6 |
| Acute myelomonocytic leukemia | 2/3 |
| Acute monocytic leukemia | 1/2 |
| Chronic myelocytic leukemia | 2/3 |
| Non-Hodgkin's lymphoma | 11/11 |

[a]Number of reactive specimens per total number of specimens tested
[b]Pre-B ALL is included in this group SN7 reacted with all 23 B chronic lymphocytic leukemia (CLL), all 6 B prolymphocytic leukemia, and all 11 non-Hodgkin's lymphoma specimens tested. Furthermore, SN7 reacted with more than 50% of the specimens tested for the following HLL; Hairy cell leukemia, non-T/non-B (including pre-B) ALL, acute myelocytic leukemia, acute myelomonocytic leukemia and chronic myelocytic leukemia. However, SN7 did not react with any of the 5 T ALL specimens tested. The reactivity of SN7 with uncultured HLL specimens is generally consistent with that of cultured cell lines (see Table 1).

FACS Analysis. Reactivity of SN7 with selected human cell specimens was investigated by FACS analysis. The results of FACS analysis were generally consistent with those of cellular IRA. The FACS analysis results are shown in FIG. 1 wherein target cells were allowed to react with SN7 or an isotype-matching control mouse IgG (MOPC 195 variant; IgG1) and stained with fluorescence-conjugated F(ab')2 of sheep anti-mouse Ig antibodies. FACS analysis was carried out using FACS 440 (Becton Dickinson). The bone marrow specimens were obtained from two different ALL patients in remission and mononuclear cells were isolated for use in the test. The B CLL specimens shown in panels C and D were from two different CLL patients. BALL-1 (a B ALL cell line) and MOLT-4 (a T ALL cell line) were used as a positive and a negative control, respectively.

Of the two normal (or near normal) bone marrow specimens derived from ALL patients in remission (panels A and B in FIG. 1), a small population (less than 10%) of mononuclear cells of one bone marrow specimen (No. 1) showed a weak but significant reaction with SN7, whereas the other bone marrow specimen (No. 2) did not show any significant reaction with SN7. For two additional normal (not involved) bone marrow specimens taken from two patients with non-Hodgkin's lymphoma, a small population (approximately 4 and 7%, respectively) of mononuclear cells showed a weak reaction with SN7. It is likely that some of the SN7 reactive cells in the above bone marrow specimens are residual malignant cells. In contrast to normal (or near normal) bone marrow cells, the majority (81 and 82%, respectively) of two B CLL cell specimens shown in FIG. 1 (panels C and D) strongly reacted with SN7. SN7 reacted strongly with virtually 100% (99%) of BALL-1 (panel E), but did not show any significant reactivity with MOLT-4 (panel F).

These FACS analysis results of normal bone marrow cells, CLL cells and cultured cell lines agreed well with the cellular RIA results of these same cell specimens (see above).

Radioimmunoprecipitation and SDS-PAGE of SN7 Antigen

Figure 2:
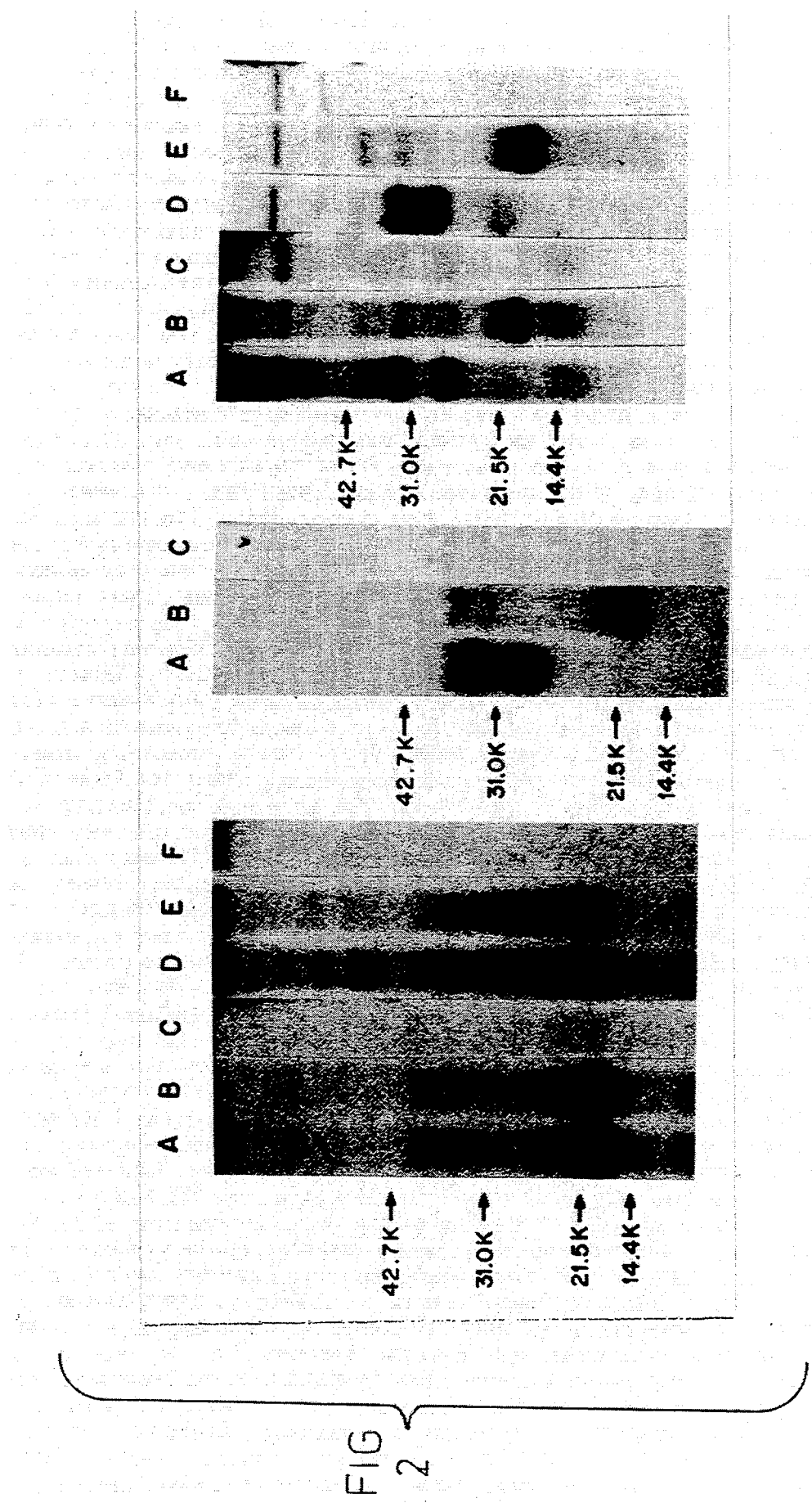
FIG. 2 depicts the results of SDS/PAGE analysis of the immunoprecipitates by SN7.

In a separate experiment where detergent extracts of cell membranes of B CLL cells were fractionated, SN7 antigen was found to bind to an LcH column. In this experiment, therefore, HLL cell-membrane glycoprotein mixtures eluted from an LcH column were used for immunoprecipitation after radiolabeling. Three samples isolated from HLL cells derived from a CLL patient, another CLL patient and two non-Hodgkin's lymphoma patients, respectively, were tested; the last sample derived from a mixture of cells from two non-Hodgkin's lymphoma patients. The immunoprecipitates obtained by using the radiolabeled samples and SN7 or an isotype-matching control mouse IgG (or control mAb) were analyzed by SDS-PAGE and autoradiographs were prepared. These results are shown in FIG. 2 wherein immunoprecipitates from $^{125}$I-labeled cell membrane glycoprotein mixtures were obtained from CLL patient a (left panel), CLL patient b (middle panel) and non-Hodgkin's lymphoma patients (right panel). The immunoprecipitation procedure used a 10-fold dilution of SN7 ascites (lanes A and D of left panel, and lanes B and E of right panel), purified SN7 antibody (lanes B and E of left panel, and lane B of middle panel), anti-HLA-DR mAb (Becton Dickinson; lane A of middle panel, and lanes A and D of right panel) and control mouse IgG (MOPC 195 variant; lanes C and F of left panel, lane C of middle panel, and lanes C and F of right panel). The immunoprecipitates were unreduced (lanes A, B and C of left and right panels) or reduced with dithiothreitol (lanes D, E and F of left and right panels and lanes A, B and C of middle panel) and analyzed by using 10% gels (left and middle panels) or 12% gels (right panel). The marker proteins (shown in K daltons) were ovalbumin (42.7), carbonic anhydrase (31.0), soybean trypsin inhibitor (21.5) and lysozyme (14.4).

The results of CLL sample a, CLL sample b and non-Hodgkin's lymphoma sample are shown in the left, middle and right panels, respectively, of FIG. 2. Under unreduced conditions, both SN7 ascites (lane A of left panel and lane B of right panel) and purified SN7 antibody (lane B of left panel) precipitated a single major radiolabeled component of approximately 20,00 daltons. Under identical conditions, an isotype-matching control mouse IgG (MOPC 195 variant; IgG1) precipitated no significant component (lanes C of left and right panels) whereas anti-HLA-DR mAb (a control mAb obtained from Becton Dickinson) precipitated α (34,000 daltons) and β(28,000 daltons) subunits of HLA-DR antigens (lane A of right panel). Under reduced conditions, both SN7 ascites (lane D of left panel and lane E of right panel) and purified SN7 antibody (lane E of left panel and lane B of middle panel) again precipitated a single major component of 20,00 daltons. Under the same reduced conditions, the control mouse IgG precipitated no significant component (lanes F of left and right panels and lane C of middle panel) whereas anti-HLA-DR mAb precipitated α and β subunits of HLA-DR antigens (lane A of middle panel and lane D of right panel). These results suggest that SN7 binds a component of a single polypeptide chain with an approximate molecular weight of 20,00. No significant difference was observed among the SN7-bound components from the three HLL samples.

Specific Cytotoxic Activity of Immunoconjugates Containing SN7

Immunoconjugates were prepared by covalently conjugating purified SN7 mAb to the A-chain subunit of ricin, a plant toxin. Ricin is composed of two disulfide-linked subunits, i.e., A and B chains. The B chain is a lectin which binds to galactose present on the surface of a wide variety of cells. The A chain is an enzyme which catalytically and irreversibly inhibits protein synthesis in the cytoplasm of the cells by acting on ribosomal RNA.

Ricin A-chain (RA) per se is not an effective cytotoxic agent against intact target cells because of its inability to bind efficiently to cell surfaces and to traverse the cell membranes. However, RA becomes effectively cytotoxic when delivered to the cytoplasm of the target cells by an appropriate delivery vehicle such as the ricin B-chain and an appropriate antibody. However, delivery of RA by ricin B-chain to target cells leads to the non-selective killing of virtually any mammalian cells because ricin B-chain binds to virtually all mammalian cells.

The cytotoxic activity of SN7 -RA conjugates against two SN7-reactive HLL cell lines, BALL-1 and NALM-6 (See Table 1), and an SN7 -nonreactive control cell line Ichikawa is summarized in Table 4.

TABLE 4

Specific cytotoxic activity of immunoconjugates prepared by conjugating purified mAb SN7 to ricin A-chain (RA) SN7-reactive BALL-1 and NALM-6 cells and SN7-nonreactive control Ichikawa cells were separately cultured in individual wells of a tissue culture plate, in triplicate, in the absence (control) or in the presence of SN7-RA conjugates ($2 \times 10^{-8}$M). The values given are the mean of triplicates ± the standard deviation.

| Cell line | SN7-RA | Viable cell number $\times 10^{-4}$ | | | | |
|---|---|---|---|---|---|---|
| | | Start | 1 day | 2 days | 3 days | 4 days |
| BALL-1 | 0 | 75 ± 0 | 105 ± 9 | 200 ± 11 | 339 ± 21 | 618 ± 41 |
| | $2 \times 10^{-8}$M | 75 ± 0 | 1.4 ± 0.6 | 0 ± 0 | 0 ± 0 | 0 ± 0 |
| NALM-6 | 0 | 75 ± 0 | 106 ± 6 | 192 ± 12 | 287 ± 11 | 514 ± 38 |
| | $2 \times 10^{-8}$M | 75 ± 0 | 25 ± 4 | 0.9 ± 0.2 | 0 ± 0 | 0 ± 0 |
| Ichikawa | 0 | 75 ± 0 | 120 ± 7 | 198 ± 10 | 291 ± 21 | 483 ± 26 |
| | $2 \times 10^{-8}$M | 75 ± 0 | 156 ± 24 | 271 ± 15 | 364 ± 21 | 472 ± 21 |

After culturing for 2 days in the presence of SN7-RA conjugates, 100% and 99.5%, respectively, of BALL -1 and NALM-6 cells were killed whereas no significant killing was observed for control Ichikawa cells. After culturing for 3 and 4 days in the presence of SN7-RA conjugates, both BALL-1 and NALM-6 cells were completely killed whereas no significant killing was observed for Ichikawa cells (see Table 3). These results clearly show that SN7-RA conjugates selectively kill HLL cells which react with SN7. Furthermore, the cytotoxic activity of SN7-RA conjugates is extremely potent compared to cytotoxic activity of RA conjugates of other mAbs, e.g., *Cancer Research* 42: 457–464 (1982) and *Cancer Research* 48: 4673–4680 (1988). RA conjugates of mAbs generally need the presence of an appropriate potentiator to effectively kill target cells e.g., *Cancer Research* 48:4673–4680 (1988).

It is important to note that SN7-RA conjugates strongly kill tumor cells in the absence of any potentiators such as $NH_4Cl$ and monensin.

Furthermore, the above test results of SN7-RA demonstrate that SN7 is effectively internalized into the target HLL cells after binding to the cell surface antigen because ricin A-chain (RA) conjugates of a mAb become efficiently cytotoxic to the intact target cells only after the conjugates are internalized into the cells through the mAb part of the conjugates.

One promising approach for the treatment of HLL is bone marrow transplantation of patients who have received aggressive high dose chemotherapy and radiotherapy. The applicability of this approach, however, has been limited because the majority of the patients do not have suitable donors of normal bone marrow. One means of overcoming this limitation is to use autologous bone marrow transplantation, provided the bone marrow from the cancer patient can be made tumor cell-free in vitro. In this regard, since the anti-HLL mAb, SN7, generated according to the process of the present invention, shows selective binding to HLL cells in vitro, but does not react or shows only minor reactivity with normal bone marrow cells, it is believed that monoclonal antibody SN7 or SN7 conjugated with one or more of the various compounds and cytotoxic agents recited earlier herein will be extremely useful for the in vitro eradication of tumor cells from the bone marrow of HLL patients.

An appropriate method of treatment for carrying out the in vitro eradication of tumor cells in leukemia/lymphoma patients using mAb SN7 or a reactive fragment of SN7 would consist of removing bone marrow aspirates from the patient to be treated containing the leukemia and/or lymphoma cells, contacting in vitro the bone marrow aspirates with the mAb or a reactive fragment of same to eradicate the leukemia and lymphoma cells, thereby rendering the aspirates essentially free of leukemia and lymphoma cells, and reintroducing the treated aspirates into the patient using known bone marrow transplantation techniques.

Another important therapeutic application of anti-HLL mAbs is their use in serotherapy. Over the past several years, a number of investigators have utilized murine mAbs for serotherapy of HLL patients by infusing or otherwise introducing a cytotoxic amount of these mAbs into such patients, as for example, through the vascular fluid and/or directly into tumor sites. Although these therapeutic attempts were, in general, not successful in inducing complete remission of the treated patients, they provided information important for designing future serotherapy protocols. Particularly, it is believed that the use of immunoconjugates rather than unconjugated naked mAbs may prove effective for overcoming many of the problems presently associated with serotherapy. As mentioned above in connection with bone marrow transplantation, drugs, toxins, radioisotopes, liposomes and many other agents may be attached directly or indirectly to appropriate anti-HLL mAbs in preparing such immunoconjugates for serotherapy.

Figure 3:
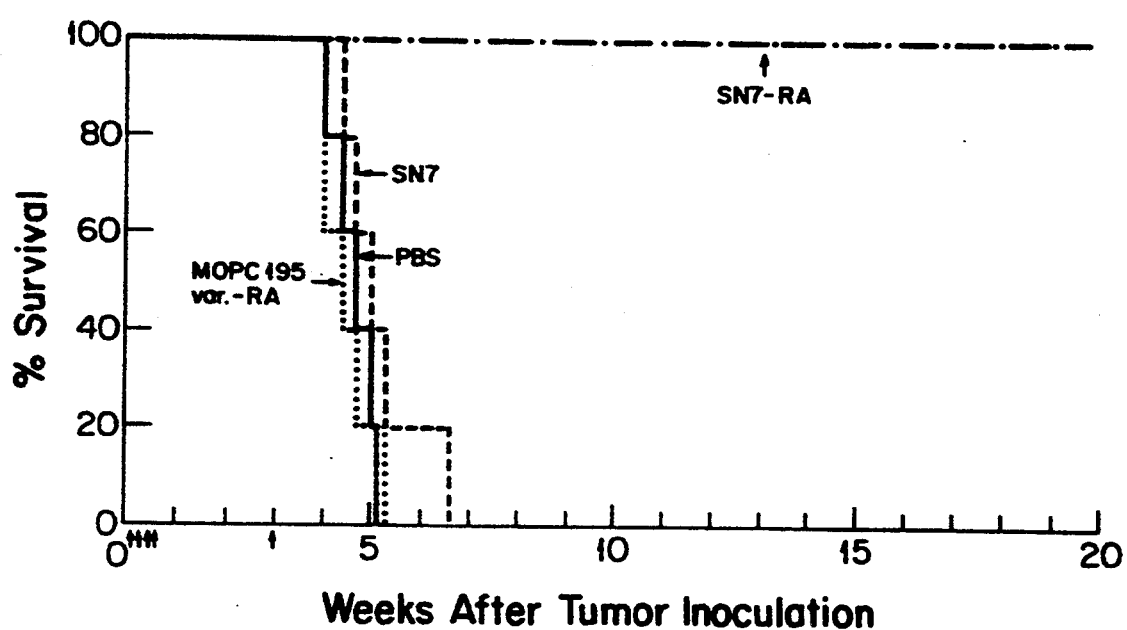
FIG. 3 depicts the in vivo therapeutic efficacy of an SN7 immunoconjugate that suppressed completely the growth of human leukemia in nude mice.

An example of such serotherapy using SN7 immunoconjugate is presented in FIG. 3. The in vivo antitumor activity of SN7-RA was evaluated using our recently established nude mouse model of NALM-6 leukemia cells [*Cancer Research* 49:706-710 (1989)]. When nude mice were inoculated i.p. with the in vivo adapted NALM-6 cells, 100% of the inoculated mice formed ascitic tumors.

Twenty nude mice each of which was inoculated with $6 \times 10^6$ in vivo adapted NALM-6 cells were divided into 4 groups and treated with PBS (control), control ricin A-chain (RA) conjugate, naked (unconjugated) mAb SN7 or SN7-RA. The results are summarized in FIG. 3.

All mice of the two control groups formed large ascitic tumors and died between 28 and 37 days after tumor inoculation. The median survival time was 32.6 and 31.4 days, respectively, for group 1 and 2 mice. Treatment of the tumor-bearing mice with naked mAb SN7 resulted in only a small increase in the survival time and the median survival time was 36.4 days (group 3 mice). In contrast, treatment with SN7-RA completely suppressed the tumor growth in all of the treated mice as long as followed, i.e., for 140 days. No sign of tumors or undesirable side effect was observed in the surviving mice.

The above results suggest strong potential of SN7-RA for serotherapy of HLL.

In addition to using the above immunoconjugates, a new type of hybrid antibody which has been genetically engineered or reshaped, called "chimeric antibodies" may also be coupled with or incorporate mAb SN7 or an active fragment thereof for use in serotherapeutic procedures. Chimeric antibodies which combine rodent mAb variable regions with human antibody constant regions have two primary advantages over the conventional animal antibodies. First, the effector functions can be selected as desired, and second, the use of human rather than animal isotypes are reported to minimize the anti-globulin responses during therapy by avoiding anti-isotypic antibodies. This technology involves incorporating the rodent antigen binding site into human antibodies by transplanting the entire variable domain or only the antigen binding site from a rodent antibody. The production of chimeric antibodies has been reported in *Proc. Natl. Acad. Sci.* USA, 31.:6851-6855 (1984), *Nature* 332:323-327 (1988) and *BioTechniques*, Volume 4 No. 3:214-220 (1986), both of which are incorporated herein by reference. Accordingly, it is further contemplated as fully within the scope of the present invention that a genetically engineered chimetic antibody incorporating the mAb disclosed herein, in whole or in part, may be successfully utilized for the treatment of a wide variety of human leukemias and lymphomas.

Still another potentially important therapeutic application of anti-HLL mAbs will be in preparing "internal image" anti-idiotype (Id) antibodies (termed Ab2β) and using Ab2β for prevention-therapy of HLL. Ab2β mimicking the original tumor associated antigen may be useful as an anti-tumor vaccine for inducing protective immunity against HLL. An idiotype or idiotypic determinant is an antigenic portion of an antibody that encompasses the variable region of the molecule. Within the variable region is the site where the antigen specifically binds to the antibody. The idiotype is often defined by an anti-idiotypic antibody (anti-Id), whereby the idiotype behaves as an antigen and induces the production of antibodies against itself.

The mechanism used to explain how an internal image anti-Id might mimic a tumor antigen and represent a vaccine is as follows. A host produces an antibody response (Ab1) against the tumor. An anti-Ab1 (or Ab2) response can be induced by immunizing appropriate animals (i.e., mice, rats, rabbits, goats, sheep, cows., horses, etc.) with Ab1. Some Ab2 which mimic the structure of the original tumor antigen may be referred to as an internal image anti-Id (Ab2β) and may be used as a substitute for the original tumor antigen. The Ab2β can be used to immunize a suitable host animal to produce an Ab3. The Ab3 can mimic the Ab1 and bind the tumor antigen. In certain instances where multi-determinant antigens are required for the induction of protective "immunity, a pool of several Ab2β may be used as the vaccine. Recently, this inventor prepared Ab2β mimicking T HLL associated antigen, termed GP37, defined by mAb SN2 as reported in *J. Immunol.* 141:1398–1403 (1988) and *J. Immunol.* 139:1354–1360 (1987), the disclosures of which are hereby incorporated by reference. This inventor also generated Ab3 mimicking mAb SN2 (Ab1) [*J. Immunol.* 141:1398–1403 (1988)], incorporated herein by reference.

Internal image anti-Id (Ab2β) antibodies may likewise be prepared by immunizing an appropriate host animal with mAb SN7 or fragments of SN7. The resulting Ab2β thus produced would mimic SN7 antigen and may have potential for inducing protective immunity against HLL in humans. In addition, the Ab2β or a fragment of same prepared using SN7 or SN7 fragments may also be used to immunize a suitable host animal to produce Ab3 antibodies mimicking the reactivity of SN7.

MAbs are also known to be highly useful for the diagnoses of various types of malignant tumors. The presence of leukemia or lymphoma cells in a patient may be determined by contacting an appropriate biological tissue cell specimen removed from the patient with a measured amount of mAbs or mAb reactive fragments and determining whether any reaction between the mAbs or fragments and the patient's cell specimen occurs using known techniques.

In particular, mAbs are currently in use for localizing antigens. Tumor radioimaging procedures are well known in the art and involve conjugating the mAb or reactive fragment of same with a labeling amount of a known radioimaging compound and introducing the labeled conjugate thus formed into the vascular fluid of a host or patient. After a sufficient length of time to allow the labeled conjugate to react with the patient's leukemia/lymphoma target cells, the patient is subjected to known scintigraphic scanning procedures to detect the location of the leukemia/lymphoma cells or tumor site(s).

MAb SN7 has been conjugated with radioactive $^{125}I$ and the resulting $^{125}I$ labeled SN7 was found to be stable. The SN7 conjugate maintained its antibody activity as demonstrated by RIA analysis.

Whole antibodies as well as reactive fragments including Fab, $F(ab')_2$, Fab' and Fv fragments may be conjugated to radioactive agents such as In-111 or I-123 to successfully identify and locate lymphoma lesions in cancer patients. Such conjugates may also be useful in therapy as radioactive agents are known to be cytotoxic to tumor cells. These techniques allow the discovery and treatment of unsuspected tumors such as those occurring in the lymph nodes.

Finally, the invention herein also contemplates providing mAb SN7 within a diagnostic kit for use in screening patients for the presence of lymphomas and leukemias. In general, such a screening procedure involves contacting an appropriate biological tissue cell specimen (i.e., blood, bone marrow, lymph node, etc.) removed from the test patient with a measured amount of mAb SN7 or a reactive fragment of SN7 and thereafter determining by known procedures whether a binding reaction between the mAb or fragment with the patient's specimen occurs. For purposes of viewing the reaction, suitable labeling agents or dyes are sometimes conjugated to the mAb or fragment. The conjugating reagent may also include one or more typical additives known in the art as, for example, buffering agents, agents for reducing background interference, and stabilizers.

When packaged as part of a diagnostic kit, suitable means may be provided within the kit for carrying out the diagnostic test. Such a kit may contain a means for obtaining the tissue cell specimen such as a syringe; the conjugated or unconjugated mAb or fragment and/or a labeling agent and ancillary agents such as slides, test tubes, etc.

The foregoing disclosure and the data presented herein demonstrate that the new mAb produced according to this invention, designated SN7, shows selective reactivity for a variety of human leukemia-lymphoma cells and its conjugate with ricin A-chain is highly potent for selective killing of human leukemia-lymphoma cells. Test results using mAb SN7 against a wide variety of malignant and normal cell specimens suggests the usefulness of SN7 in the diagnosis and treatment of cancer patients suffering from a wide variety of leukemia-lymphomas.

The cell line designated T6-1G9, was deposited on May 18, 1989 at the American Type Culture Collection, 12301 Parklawn Drive, Rockville, Md. 20852 U.S.A. and was assigned the ATCC accession number HB 10151.

Although specific embodiments of the invention have been described herein for purposes of illustration, various modifications may be apparent to those skilled in the art without deviating from the spirit and scope of this invention. It is therefore intended that the present invention be limited only by the scope of the appended claims.

What is claimed is:

1. A leukemia lymphoma reactive monoclonal antibody which reacts with human B chronic lymphocytic leukemia cells; B prolymphocytic leukemia cells; Hairy cell leukemia cells; non-T/non-B acute lymphoblastic leukemia cells; B acute lymphoblastic leukemia cells; acute myelocytic leukemia cells; acute myelomonocytic leukemia cells; acute monocytic leukemia cells; chronic myelocytic leukemia cells and non-Hodgkin's lymphoma cells; said monoclonal antibody being produced by a hybridoma cell line designated T6-1G9 (ATCC HB 10151) generated by fusing mouse myeloma cells with spleen cells from a suitable animal immunized with a non-T/non-B (B lineage) leukemia antigen preparation isolated from cell membranes of human acute lymphoblastic leukemia cells.

2. A hybridoma cell line designated T6-1G9, having the deposit accession number ATCC HB 10151.

* * * * *